United States Patent
Zhang et al.

(10) Patent No.: US 11,476,102 B2
(45) Date of Patent: Oct. 18, 2022

(54) REAL-TIME CALIBRATION DEVICE, REAL-TIME CALIBRATION METHOD AND DETECTION APPARATUS

(71) Applicants: Nuctech Company Limited, Beijing (CN); Tsinghua University, Beijing (CN)

(72) Inventors: Qingjun Zhang, Beijing (CN); Zhiqiang Chen, Beijing (CN); Yuanjing Li, Beijing (CN); Jianmin Li, Beijing (CN); Yinong Liu, Beijing (CN); Yaohong Liu, Beijing (CN); Guangqin Li, Beijing (CN); Weiping Zhu, Beijing (CN); Ge Li, Beijing (CN); Qiufeng Ma, Beijing (CN); Biao Cao, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 16/947,998

(22) Filed: Aug. 27, 2020

(65) Prior Publication Data

US 2021/0118656 A1   Apr. 22, 2021

(30) Foreign Application Priority Data

Oct. 16, 2019   (CN) .......................... 201910981918.1

(51) Int. Cl.
*H01J 49/00* (2006.01)
*G01N 27/622* (2021.01)
*H01J 49/04* (2006.01)

(52) U.S. Cl.
CPC ........ *H01J 49/0009* (2013.01); *G01N 27/622* (2013.01); *H01J 49/0495* (2013.01)

(58) Field of Classification Search
CPC ............... H01J 49/0009; H01J 49/0027; H01J 49/0031; H01J 49/02; H01J 49/0495; G01N 27/622; G01N 33/0006
(Continued)

(56) References Cited

U.S. PATENT DOCUMENTS 4,298,795 A * 11/1981 Takeuchi ............... H01J 49/045
250/288
4,399,942 A * 8/1983 Chand ................ G01N 33/0006
239/34

(Continued)

FOREIGN PATENT DOCUMENTS

CN         106645513         5/2017

OTHER PUBLICATIONS

"Chinese Application Serial No. 201910981918.1, Office Action dated Oct. 18, 2021", (Oct. 18, 2021), 8 pgs.

*Primary Examiner* — Jason L McCormack
(74) *Attorney, Agent, or Firm* — Schwegman Lundberg & Woessner, P.A.

(57) ABSTRACT

Embodiments of the present disclosure provide a real-time calibration device, a real-time calibration method and a detection apparatus. The real-time calibration device is in fluid communication with a sample injection pipeline of the apparatus to be calibrated. The real-time calibration device is configured to release a trace amount of calibration agent molecules during a sample injection of the apparatus to be calibrated, so that the trace amount of calibration agent molecules and a sample entering the apparatus to be calibrated are mixed and together enter the apparatus to be calibrated, and information of the sample and the calibration agent is detected by the apparatus to be calibrated, thereby performing a calibration.

14 Claims, 1 Drawing Sheet

(58) Field of Classification Search
USPC .................................... 250/281, 282, 288
See application file for complete search history.

(56) References Cited

U.S. PATENT DOCUMENTS

| | | | |
|---|---|---|---|
| 6,593,567 | B1 | 7/2003 | Abdel-rahman |
| 9,153,423 | B2 | 10/2015 | Beil et al. |
| 10,699,887 | B2 | 6/2020 | Zhang et al. |
| 2009/0166524 | A1* | 7/2009 | Geraghty ............. G01N 27/622 |
| | | | 250/282 |
| 2012/0138783 | A1* | 6/2012 | Peng ................... G01N 27/622 |
| | | | 250/288 |
| 2016/0133449 | A1* | 5/2016 | Burton ................. G01N 27/622 |
| | | | 250/288 |
| 2018/0158659 | A1 | 6/2018 | Zhang et al. |

* cited by examiner

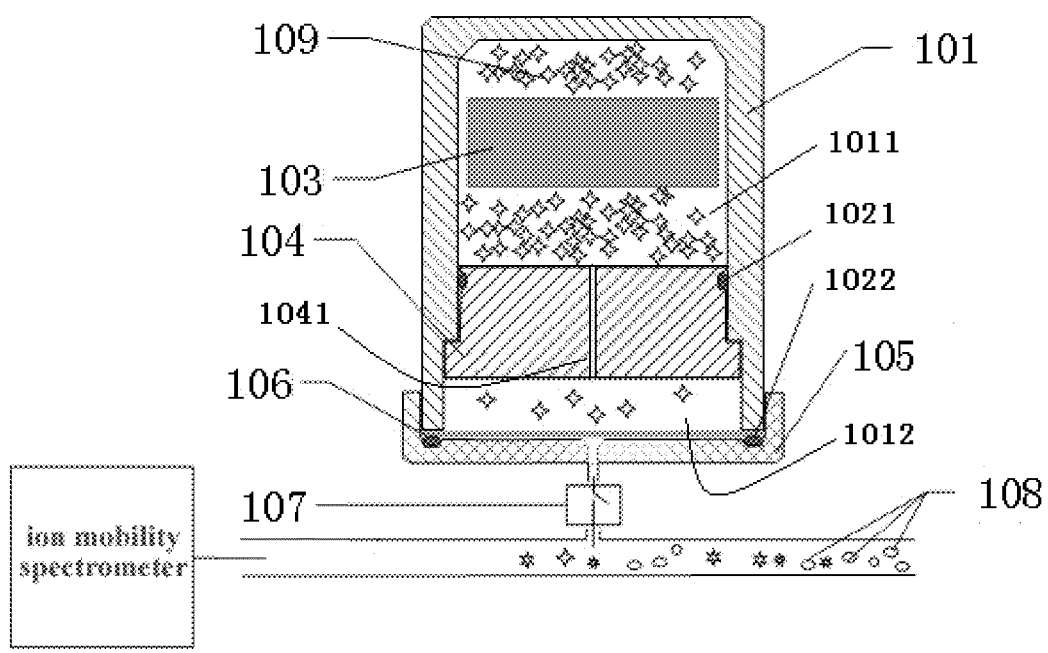

REAL-TIME CALIBRATION DEVICE, REAL-TIME CALIBRATION METHOD AND DETECTION APPARATUS

CROSS REFERENCE TO RELATED APPLICATIONS

This application claims priority to the Chinese Patent Application No. 201910981918.1 filed on Oct. 16, 2019, which is incorporated herein by reference in its entirety.

TECHNICAL FIELD

Embodiments of the present disclosure relate to the application fields of drugs, explosives, chemical warfare agents, industrial hazardous chemicals, and inspection and quarantine, and in particular to a real-time calibration device, a real-time calibration method and a detection apparatus.

BACKGROUND

Ion mobility spectrometry (IMS) has the advantages of portability, rapidness, sensitivity and industrialization, and is widely used in fields of military, national defense, industry, environment and clinical diagnosis. However, due to the interference of other complex substrates such as water vapor in the detection environment, its qualitative and quantitative ability is greatly limited.

SUMMARY

One aspect of the present disclosure provides a real-time calibration device used for an apparatus to be calibrated, including: a calibration agent storage tank for storing a calibration agent; a sealing plug arranged in the calibration agent storage tank to divide a space therein into a first cavity and a second cavity, the sealing plug including one or more capillary through holes to allow calibration agent molecules stored in the first cavity to diffuse into the second cavity through the one or more capillary through holes of the sealing plug; and a valve configured to open or close a passage between the second cavity of the calibration agent storage tank and a sample injection pipeline of the apparatus to be calibrated, so as to control a release of the calibration agent into the sample injection pipeline of the apparatus to be calibrated; wherein the valve is connected to the sample injection pipeline of the apparatus to be calibrated.

In an embodiment, the valve is an electromagnetic valve configured to open for a predetermined period of time during a sample injection of the apparatus to be calibrated, so that the calibration agent storage tank instantaneously releases a trace amount of calibration agent into the sample injection pipeline, the trace amount of calibration agent and a sample entering the apparatus to be calibrated are mixed and together enter the apparatus to be calibrated, and information of the sample and the calibration agent is detected by the apparatus to be calibrated, thereby performing a calibration.

In an embodiment, the real-time calibration device includes a storage tank cover connected to the storage tank and covering one end of the storage tank, and the valve is in fluid communication with the storage tank through a through hole provided in the storage tank cover.

In an embodiment, the real-time calibration device includes a semi-permeable membrane arranged on one end of the storage tank close to the valve, the semi-permeable membrane and the sealing plug define the second cavity, and the semi-permeable membrane allows the calibration agent molecules to enter the valve from the second cavity through the semi-permeable membrane.

In an embodiment, the real-time calibration device includes a calibration agent capsule arranged in the first cavity to store a calibration agent-contained sample so as to enable a release of the calibration agent molecules into the first cavity.

In an embodiment, the real-time calibration device includes a first O-ring washer arranged between the sealing plug and an inner wall of the storage tank, so as to seal a gap between the sealing plug and the inner wall of the storage tank.

In an embodiment, the real-time calibration device includes a second O-ring washer arranged between the storage tank cover and an end surface of the storage tank at one end, so as to seal the storage tank.

Another aspect of the present disclosure provides a real-time calibration method used for an apparatus to be calibrated, including:

releasing a trace amount of calibration agent molecules during a sample injection of the apparatus to be calibrated, so that the trace amount of calibration agent molecules and a sample entering the apparatus to be calibrated are mixed and together enter the apparatus to be calibrated, and information of the sample and the calibration agent is detected by the apparatus to be calibrated, thereby performing a calibration on the apparatus.

In an embodiment, the trace amount of calibration agent molecules is released instantaneously by using a calibration device, wherein the calibration device includes: a calibration agent storage tank for storing a calibration agent; and a valve configured to open or close a passage between the calibration agent storage tank and a sample injection pipeline of the apparatus to be calibrated, so as to control a release of the calibration agent molecules into the sample injection pipeline of the apparatus to be calibrated; wherein the real-time calibration method includes: during a sample injection of the apparatus to be calibrated, opening the valve for a predetermined period of time to release the calibration agent molecules, so that the calibration agent molecules and the sample molecules are mixed and together enter the apparatus to be calibrated.

In an embodiment, the calibration device further includes a sealing plug arranged in the calibration agent storage tank to divide a space therein into a first cavity and a second cavity, and the sealing plug includes one or more capillary through holes to allow calibration agent molecules stored in the first cavity to diffuse into the second cavity through the one or more capillary through holes of the sealing plug.

In an embodiment, the calibration device further includes a storage tank cover (105) connected to the calibration agent storage tank and covering one end of the calibration agent storage tank, and the valve is in fluid communication with the storage tank through a through hole provided in the storage tank cover.

In an embodiment, the calibration device further includes a semi-permeable membrane (106) arranged on one end of the calibration agent storage tank close to the valve, the semi-permeable membrane and the sealing plug define the second cavity, and the semi-permeable membrane allows the calibration agent molecules to enter the valve from the second cavity through the semi-permeable membrane.

In an embodiment, the calibration device further includes a calibration agent capsule (103) arranged in the first cavity and comprising a capsule shell and the calibration agent contained in the capsule shell, the capsule shell allowing the calibration agent capsule to release calibration agent molecules into the first cavity.

In an embodiment, the calibration device further includes a first O-ring washer arranged between the sealing plug and an inner wall of the storage tank, so as to seal a gap between the sealing plug and the inner wall of the storage tank.

In an embodiment, the calibration device further includes a second O-ring washer arranged between the storage tank cover and an end surface of the storage tank at one end, so as to seal the storage tank.

In an embodiment, during an input of sample molecules (108) of the apparatus to be calibrated, the valve is opened for a predetermined period of time to release the calibration agent molecules, so that the calibration agent molecules and the sample molecules are mixed and together enter the apparatus to be calibrated.

The real-time calibration method further includes:

obtaining measured peak position information $t_{x\ sample}$ of the sample and calibration agent peak position information $t_1$;

extracting current calibration agent peak position information $t_{c1}$, comparing it with reference calibration agent peak position information $t_{c0}$ stored in a database, and calculating a ratio $C_i=(t_{c0})/(t_{c1})$ of the reference calibration agent peak position information $t_{c0}$ to the current calibration agent peak position information $t_{c1}$; and multiplying the ratio $C_i$ by the measured peak position information $t_{x\ sample}$ of the sample, and obtaining a calibrated peak position $t_{sample}$ of the sample.

Yet another aspect of the present disclosure provides a detection apparatus comprising a measurement device and the above-mentioned real-time calibration device, wherein the measurement device is the above-mentioned apparatus to be calibrated, and wherein the real-time calibration device is in fluid communication with a sample injection pipeline of the measurement device through the valve.

In an embodiment, during a sample injection of the measurement device, the real-time calibration device instantaneously releases a trace amount of calibration agent molecules, the trace amount of calibration agent molecules and a sample are mixed and together enter the measurement device, and information of the sample and the calibration agent is detected by the measurement device, thereby performing a calibration on the measurement device.

In an embodiment, the measurement device is configured to:

obtain measured peak position information $t_{x\ sample}$ of the sample and calibration agent peak position information $t_{c1}$;

extract current calibration agent peak position information $t_{c1}$, compare it with reference calibration agent peak position information $t_{c0}$ stored in the database, and calculate a ratio $C_i=(t_{c0})/(t_{c1})$ of the reference calibration agent peak position information $t_{c0}$ to the current calibration agent peak position information $t_{c1}$; and multiply the ratio $C_i$ by the measured peak position information $t_x$ sample of the sample, and obtain a calibrated peak position $t_{sample}$ of the sample.

Yet another aspect of the present disclosure provides an ion mobility spectrometer apparatus including an ion mobility spectrometer and the above-mentioned real-time calibration device, wherein the real-time calibration device is in fluid communication with a sample injection pipeline of the ion mobility spectrometer through the valve.

BRIEF DESCRIPTION OF THE ACCOMPANYING DRAWINGS

FIG. 1 shows a diagram of a real-time calibration device according to an embodiment of the present disclosure.

DETAILED DESCRIPTION

The technical solutions in the embodiments of the present disclosure will be described clearly and completely in conjunction with the drawings in the embodiments of the present disclosure. Obviously, the described embodiments are only a part of the embodiments of the present disclosure, but not all the embodiments. The following description of at least one exemplary embodiment is actually merely illustrative, and in no way serves as any limitation to the present disclosure and its application or use. Based on the embodiments of the present disclosure, all other embodiments obtained by those ordinary skilled in the art without carrying out creative work fall within the protection scope of the present disclosure.

Techniques, methods and equipment known to those ordinary skilled in the related art may not be discussed in detail, but where appropriate, the techniques, methods and equipment should be considered as part of the authorized specification.

In the description of the present disclosure, it should be understood that the orientation or positional relationship indicated by the orientation words "front", "back", "upper", "lower", "left", "right", ""vertical", "horizontal", "top", "bottom" and others is based on the orientation or positional relationship shown in the drawings, to facilitate the description of the present disclosure and simplify the description, rather than to indicate or imply that the device or element referred to must have a specific orientation or to be constructed and operated in a specific orientation, and cannot therefore be understood as a limitation of the present disclosure. The orientation words "inside" and "outside" refer to the inside and outside relative to the contour of each component itself.

In the description of this disclosure, it should be understood that the use of "first", "second" and other words to define parts is only to facilitate the distinction between the corresponding parts, and unless otherwise stated, the above words are not special Meaning, and therefore cannot be understood as a limitation to the protection scope of the present disclosure.

Ion mobility spectrometer identifies substances based on different mobility rates of various substances. However, mobility time of substances is directly related to the operating environment of the instrument, such as temperature, air pressure, and humidity. The same substance has different mobility time under different temperature, humidity or air pressure. Therefore, the ion mobility spectrometer must calibrate the mobility time according to the operating environment, especially the air pressure, to ensure the correct use of the instrument.

Calibration of a traditional ion mobility detector is to dissolve calibration material with an organic solvent and dilute it into a low-concentration standard solution, then take a small amount of standard solution and add it to the sampling paper, and after the solvent evaporates, insert the sampling paper into the injection port of the instrument for detection. However, this type of calibration device requires a separate entity, which is not convenient to carry. Moreover, because the calibration and the test are not synchronous, the current calibration is difficult to truly apply to the entire test process.

In addition, another type of calibration scheme is to set up a calibration branch in the internal circulation gas path of the ion mobility spectrometer. When the instrument needs to be calibrated, the calibration gas path valve is opened, and a trace amount of calibration agent is loaded into the ion mobility spectrometer by carrier gas. After calibration peak position and calibration coefficient are obtained, the calibration is performed. Then the calibration gas path valve is closed, and the sample is measured. The measurement result of the sample is calibrated with the calibration result. Such a measurement method increases the complexity of the entire gas path, and the calibration circuit may be different from the detection apparatus, resulting in system errors.

The embodiments according to the present disclosure will be described below with reference to the accompanying drawings.

The embodiments of the present disclosure provide a real-time calibration device, which is in fluid communication with the sample injection pipeline of the apparatus to be calibrated.

The real-time calibration device is configured to instantaneously release a trace amount of calibration agent molecules during a sample injection of the apparatus to be calibrated, so that the trace amount of calibration agent molecules and the sample are mixed and together enter the apparatus to be calibrated, and information of the sample and the calibration agent is detected by the apparatus to be calibrated, thereby performing a calibration. Here, it should be understood that the real-time calibration device is located upstream of the measurement device in the apparatus to be calibrated, so that the calibration agent enters the measurement device for measurement.

In an embodiment, the real-time calibration device used for an apparatus to be calibrated or a system to be calibrated includes: a calibration agent storage tank 101 for storing a calibration agent; a sealing plug 104 arranged in the calibration agent storage tank 101 to divide a space therein into a first cavity 1011 and a second cavity 1012, the sealing plug 104 including one or more capillary through holes to allow calibration agent molecules 109 stored in the first cavity 1011 to diffuse into the second cavity 1012 through the one or more capillary through holes 1041 of the sealing plug 104; and a valve 107 configured to open or close a passage between the second cavity 1012 of the calibration agent storage tank 101 and a sample injection pipeline of the apparatus to be calibrated, so as to control a release of the calibration agent into the sample injection pipeline of the apparatus to be calibrated. In the present embodiment, the valve 107 is connected to the sample injection pipeline of the apparatus to be calibrated. The real-time calibration device is configured so that the calibration agent storage tank 101 instantaneously releases a trace amount of calibration agent during the sample injection of the apparatus to be calibrated, the trace amount of calibration agent and the sample are mixed and together enter the apparatus to be calibrated, and information of the sample and the calibration agent is detected by the apparatus to be calibrated, thereby performing a calibration.

According to the present embodiment, the real-time calibration device is in fluid communication with the sample injection pipeline of the apparatus to be calibrated, the trace amount of calibration agent and the sample are mixed and together enter the apparatus to be calibrated, then the information of the sample and the calibration agent is detected by the apparatus to be calibrated. Therefore, no separate or additional devices or circuits are needed in the calibration process, the calibration agent and the sample are measured under the same measurement environment, and the calibration is more objective and accurate. The trace amount of calibration agent here is a common concept in the art. Those skilled in the art may determine the specific amount of the trace according to the specific device and technical scheme.

In an embodiment, in order to achieve the delivery of the calibration agent, the real-time calibration device includes a valve 107. When the calibration is performed, the valve 107 opens the passage between the calibration agent storage tank 101 and the sample injection pipeline of the apparatus to be calibrated, so that the calibration agent in the calibration agent storage tank 101 enters the sample injection pipeline of the apparatus to be calibrated through the valve 107, and is then mixed and measured together with the sample. In an embodiment, the valve 107 may be an electromagnetic on-off valve 107, which may be quickly opened or closed, and thus can be used to control the time for adding the calibration agent and the amount of the added calibration agent. During the sampling/injection of the apparatus to be calibrated, the electromagnetic on-off valve 107 in fluid communication with the calibration agent storage tank 101 and the sample injection pipeline is opened for several microseconds (μs) or milliseconds (ms). A trace amount of calibration agent molecules 109 stored in the calibration agent storage tank 101 enters the sampling/injection pipeline of the apparatus to be calibrated through the electromagnetic on-off valve 107. Then the trace amount of calibration agent molecules 109 and sample molecules 108 (indicated by ellipse in the figure) are mixed and detected together, and peak position information is obtained. The electromagnetic on-off valve 107 can achieve fast and accurate switching operations. The amount of calibration agent molecules 109 (indicated by stars in the figure) entering the sample injection pipeline may be controlled by ON duration of the electromagnetic on-off valve 107.

In an embodiment, the real-time calibration device further includes a storage tank cover 105 connected to the storage tank 101 and covering one end of the storage tank 101, and the valve 107 is in fluid communication with the storage tank 101 through a through hole provided in the storage tank cover 105. In another embodiment, the storage tank 101 may be an integral structure.

In an embodiment, the real-time calibration device may include a sealing plug 104 arranged in the calibration agent storage tank 101 to divide the space therein into a first cavity 1011 and a second cavity 1012. In the present embodiment, the real-time calibration device further includes a calibration agent capsule 103 arranged in the first cavity 101 to store a calibration agent-contained sample so as to enable a release of the calibration agent molecules 109 into the first cavity 1011. The calibration agent capsule 103 is a calibration agent-contained capsule, with a capsule shell allowing the calibration agent molecules 109 to diffuse from the inside of the capsule shell to the outside of the capsule shell.

The arrangement of the calibration agent capsule 103 is advantageous. The capsule shell can contain the calibration agent sample, but only the calibration agent molecules 109 are allowed to diffuse out of the calibration agent capsule 103. In other words, the calibration particles cannot diffuse out of the calibration agent capsule 103. Therefore, the calibration agent will not contaminate the real-time calibration device or other components, and the release of the calibration agent molecules 109 becomes controllable. Moreover, the calibration agent stored in the capsule shell can release calibration agent molecules 109 for a long time, so that a calibration agent capsule 103 can have a long life, avoiding frequent replacement or replenishment of the calibration agent.

The arrangement of the sealing plug 104 is advantageous because two cavities can be obtained in the space within the calibration agent storage tank 101 through the sealing plug 104, and the density of the calibration agent molecules 109 in the second cavity 1012 is much smaller than that in the first cavity 1011. In other words, the amount of the calibration agent released into the second cavity 1012 and then delivered to the apparatus to be calibrated may be controlled by the sealing plug 104. Specifically, the speed at which the calibration agent molecules 109 diffuse from the first cavity 1011 to the second cavity 1012 may be controlled by the number and size of the capillary through holes 1041 in the sealing plug 104, thereby controlling the density of the calibration agent molecules 109 in the second cavity 1012, and further, in cooperation with the valve 107, controlling the extremely small amount of calibration agent molecules 109 delivered to the apparatus to be calibrated. In an embodiment, the sealing plug 104 may be a polytetrafluoroethylene sealing plug 104 with one or more capillary through holes 1041 opened therein. In the present embodiment, a two-stage deceleration effect on the diffusion of the calibration agent molecules 109 can be obtained by the capsule shell and the sealing plug 104.

In an embodiment, the real-time calibration device further includes a semi-permeable membrane 106 arranged on one end of the calibration agent storage tank 101 close to the valve 107. The semi-permeable membrane 106 and the sealing plug 104 define the second cavity 1012. The semi-permeable membrane 1016 allows the calibration agent molecules 109 to enter the valve 107 from the second cavity 1012 through the semi-permeable membrane 106. The semi-permeable membrane 106 functions to, while allowing the calibration agent molecules 109 to enter the sample injection flow path of the apparatus to be calibrated from the second cavity 1012, prevent external molecules from entering the second cavity 1012. For example, it may prevent the sample molecules 108 or carrier gas molecules in the sample injection flow path from entering the second cavity 1012 to contaminate the calibration agent. Moreover, the calibration agent molecules 109 pass through the semi-permeable membrane 106 under the driving of a concentration gradient, which may further control the speed at which the calibration agent molecules 109 is delivered into the sample injection flow path of the apparatus to be calibrated. Therefore, in the present embodiment, a multi-stage deceleration effect on the delivery of the calibration agent molecules 109 can be obtained through the capsule shell, the sealing plug 104 and the semi-permeable membrane 106, thereby achieving the release of a trace amount of calibration agent molecules 109.

It should be known that the semi-permeable membrane 106 is not necessary. In an embodiment, the sealing plug 104 may define the second cavity 1012 with the storage tank cover 105. That is to say, the calibration agent molecules 109 can enter the sample injection flow path of the apparatus to be calibrated from the second cavity 1012 directly through the valve 107.

In an embodiment, the real-time calibration device does not include the sealing plug 104, that is, the calibration agent storage tank 101 is not provided with the sealing plug 104, but only with the semi-permeable membrane 106. The amount of calibration agent delivered is accurately controlled by the electromagnetic on-off valve 107, so as to achieve the delivery of the trace amount of calibration agent molecules 109.

In an embodiment, the real-time calibration device may include a first O-ring washer arranged between the sealing plug 104 and the inner wall of the calibration agent storage tank 101, so as to seal a gap between the sealing plug 104 and the inner wall of the calibration agent storage tank 101.

In an embodiment, the real-time calibration device may include a second O-ring washer arranged between the calibration agent storage tank cover 105 and an end surface of the calibration agent storage tank 101 at one end, so as to seal the calibration agent storage tank 101.

The embodiments of the present disclosure further provide a real-time calibration method used for an apparatus to be calibrated. The real-time calibration method includes: releasing a trace amount of calibration agent molecules 109 during a sample injection of the apparatus to be calibrated, so that the trace amount of calibration agent molecules 109 and the sample of the apparatus to be calibrated are mixed and together enter the apparatus to be calibrated, and information of the sample and the calibration agent is detected by the apparatus to be calibrated, thereby performing a calibration.

In an embodiment, the trace amount of calibration agent molecules 109 may be released by using a calibration device. Specifically, the calibration device may include: a calibration agent storage tank 101 for storing a calibration agent, and a valve 107 configured to open or close a passage between the calibration agent storage tank 101 and a sample injection pipeline of the apparatus to be calibrated, so as to control a release of the calibration agent molecules 109 into the sample injection pipeline of the apparatus to be calibrated. The real-time calibration method includes: during the sample injection of the apparatus to be calibrated, opening the valve 107 for a predetermined period of time, for example, ranging from 10 microseconds to 1000 milliseconds, which may be determined according to actual needs and the concentration of calibration agent molecules, to release the calibration agent molecules 109, so that the calibration agent molecules 109 and the sample molecules 108 are mixed and together enter the apparatus to be calibrated.

In an embodiment, the calibration device further includes a sealing plug 104 arranged in the calibration agent storage tank 101 to divide a space therein into a first cavity 1011 and a second cavity 1012. The sealing plug 104 includes one or more capillary through holes 1041 to allow the calibration agent molecules 109 stored in the first cavity 1011 to diffuse into the second cavity 1012 through the one or more capillary through holes 1041 of the sealing plug 104.

In an embodiment, the calibration device further includes a semi-permeable membrane 106 arranged on one end of the calibration agent storage tank 101 close to the valve 107. The semi-permeable membrane 106 and the sealing plug 104 define the second cavity 1012. The semi-permeable membrane 106 allows the calibration agent molecules 109 to enter the valve 107 from the second cavity 1012 through the semi-permeable membrane 106.

The arrangement of the sealing plug 104 or the semi-permeable membrane 106 is advantageous. Specifically, two cavities can be obtained in the space within the calibration agent storage tank 101 through the sealing plug 104, and the density of the calibration agent molecules 109 in the second cavity 1012 is much smaller than that in the first cavity 1011. In other words, the amount of the calibration agent released into the second cavity 1012 may be controlled by the sealing plug 104, thereby further controlling the amount of the calibration agent delivered to the apparatus to be calibrated. Specifically, the speed at which the calibration agent molecules 109 diffuse from the first cavity 1011 to the second cavity 1012 may be controlled by the number and size of the capillary through holes 1041 in the sealing plug 104, thereby controlling the density of the calibration agent molecules 109 in the second cavity 1012, and further, in cooperation with the valve 107, controlling the extremely small amount of calibration agent molecules 109 delivered to the apparatus to be calibrated. In an embodiment, the sealing plug 104 may be a polytetrafluoroethylene sealing plug 104 with one or more capillary through holes 1041 opened therein. In the present embodiment, a two-stage deceleration effect on the diffusion of the calibration agent molecules 109 can be obtained by the capsule shell and the sealing plug 104. In the embodiment where the semi-permeable membrane 106 is used, the speed at which the calibration agent molecules pass through the semi-permeable membrane 106 is greatly slowed down. By combining with the control of the valve 107, the release of the trace amount of calibration agent molecules 109 can be achieved. In the embodiment where the sealing plug 104 and the semi-permeable membrane 106 are used simultaneously, the release of the trace amount of calibration agent molecules 109 can be achieved more easily and accurately.

In an embodiment, the calibration agent capsule 103 may be used. It is placed in the first cavity 1011 to store a calibration agent-contained sample so as to enable a release of the calibration agent molecules 109 into the first cavity 1011. The calibration agent capsule 103 is an individual capsule for containing the calibration agent with a capsule shell. The capsule shell allows the calibration agent molecules 109 to diffuse from the inside of the capsule to the outside of the calibration agent capsule 103, while preventing macroscopic calibration agent particles or powders from passing through the capsule shell. The capsule shell can be formed of any material with nano-scale pores. For example, the size of the pores in the capsule shell ranges from 0.1 nm to 100 nm, so that nano-scale calibration agent molecules can pass through the pores in the capsule shell to penetrate or diffuse from the space inside the capsule shell with high concentration of calibration agent molecules to the space outside the capsule shell with relatively low concentration of calibration agent molecules. It should be known that the structure of the capsule shell here allows the molecules inside and outside the capsule shell to penetrate or diffuse from the higher concentration side to the lower concentration side under the driving of the concentration gradient. The penetration or diffusion of molecules is completely driven by the concentration gradient, without the need to provide other external forces. The arrangement of the calibration agent capsule 103 is advantageous. The capsule shell can contain the calibration agent sample, but only the calibration agent molecules 109 are allowed to diffuse out of the calibration agent capsule 103, and the (macroscopic) calibration agent particles or powders can be hold stably. In other words, the calibration agent particles or powders cannot leak out of the calibration agent capsule 103. Therefore, there is no risk of contamination of the real-time calibration device or other components by the calibration agent, and the release of the calibration agent molecules 109 becomes stable and controllable. In addition, the calibration agent stored in the capsule shell 103 can release calibration agent molecules 109 for a long time, so that a calibration agent capsule 103 can have a long life, avoiding frequent replacement or replenishment of the calibration agent.

In an embodiment, the calibration device further includes a first O-ring washer 1021 arranged between the sealing plug 104 and the inner wall of the calibration agent storage tank 101, so as to seal a gap between the sealing plug 104 and the inner wall of the calibration agent storage tank 101. The calibration device further includes a second O-ring washer 1012 arranged between the storage tank cover 105 and an end surface of the calibration agent storage tank 101 at one end, so as to seal the calibration agent storage tank 101.

In an embodiment, during the input of the sample molecules 108 of the apparatus to be calibrated, the valve 107 is opened for a predetermined period of time (on the order of microseconds or milliseconds) to release the calibration agent molecules 109, so that the calibration agent molecules 109 and the sample molecules 108 are mixed and together enter the apparatus to be calibrated. When the calibration agent molecules 109 enter the apparatus to be calibrated, the method includes obtaining measured peak position information $t_{x\ sample}$ of the sample and calibration agent peak position information $t_{c1}$. For example, the peak position information $t_{c1}$ of the calibration agent molecules 109 can be measured while the peak position information $t_{x\ sample}$ is measured by the measuring device in the apparatus to be calibrated. The trace amount of calibration agent molecules 109 has no effect on the measured peak position information $t_{x\ sample}$ of the sample, and the calibration agent peak position information $t_{c1}$ can be measured by the measurement device in the apparatus to be calibrated.

The method further includes calibrating the measured peak position of the sample by using the peak position information $t_{c1}$ of the calibration agent molecules 109. Specifically, the method includes extracting current calibration agent peak position information $t_{c1}$, comparing it with reference calibration agent peak position information $t_{c0}$ stored in a database, and calculating a ratio $C_i = (t_{c0})/(t_{c1})$ of the reference calibration agent peak position information $t_{c0}$ to the current calibration agent peak position information $t_{c1}$.

The method further includes multiplying the ratio $C_i$ by the measured peak position information $t_{x\ sample}$ of the sample, and obtaining a calibrated peak position $t_{sample}$ of the sample.

The embodiments of the present disclosure further provide a detection apparatus, including a measurement device and the above-mentioned real-time calibration device. In the present embodiment, the real-time calibration device is in fluid communication with the sample injection pipeline of the detection apparatus through the valve 107. During general operations of the detection apparatus, the valve 107 of the real-time calibration device may be in OFF state, and the detection apparatus performs normal operations such as sample detection. During the calibration, the valve 107 is opened, and a trace amount of calibration agent molecules 109 enters the detection apparatus. The trace amount of calibration agent molecules and the sample molecules 108 are mixed and delivered together to the measurement device in the detection apparatus for measurement, thereby calibrating the detection apparatus.

The measurement device in the detection apparatus is configured to: obtain measured peak position information $t_{x\ sample}$ of the sample and calibration agent peak position information $t_{c1}$; extract current calibration agent peak position information $t_{c1}$, compare it with reference calibration agent peak position information $t_{c0}$ stored in the database, and calculate a ratio $C_i = (t_{c0})/(t_{c1})$ of the reference calibration agent peak position information $t_{c0}$ to the current calibration agent peak position information $t_{c1}$; and multiply the ratio $C_i$ by the measured peak position information $t_x$ sample of the sample, and obtain a calibrated peak position $t_{sample}$ of the sample.

The embodiments of the present disclosure further provide an ion mobility spectrometer apparatus, including an ion mobility spectrometer and the above-mentioned real-time calibration device, wherein the real-time calibration device is in fluid communication with the sample injection pipeline of the ion mobility spectrometer through the valve 107.

In an embodiment, during general operations of the ion mobility spectrometer apparatus, the valve 107 of the real-time calibration device may be in OFF state. When the sample is measured by the ion mobility spectrometer, the valve 107 is opened, and the calibration agent molecules 109 enter the sample injection pipeline of the ion mobility spectrometer apparatus. The calibration agent molecules and the sample molecules 108 are mixed and delivered together to the ion mobility spectrometer apparatus for measurement. The ion mobility spectrometer apparatus is configured to: obtain measured peak position information $t_{x\ sample}$ of the sample and calibration agent peak position information $t_{c1}$; extract current calibration agent peak position information $t_{c1}$, compare it with reference calibration agent peak position information $t_{c0}$ stored in the database, and calculate a ratio $C_i=(t_{c0})/(t_{c1})$ of the reference calibration agent peak position information $t_{c0}$ to the current calibration agent peak position information $t_1$; and multiply the ratio $C_i$ by the measured peak position information $t_{x\ sample}$ of the sample, and obtain a calibrated peak position $t_{sample}$ of the sample.

The ion mobility spectrometer apparatus of the embodiments of the present disclosure may perform real-time calibration of the ion mobility spectrometer apparatus under the condition of sample measurement. The icon mobility spectrometer apparatus may be calibrated without additional tools or systems, or even without separate calibration of the ion mobility spectrometer apparatus before the sample measurement and calibration of measurement results. According to the ion mobility spectrometer apparatus of the embodiments of the present disclosure, the initial environments of the calibration agent and the sample under test are the same, and the various detection conditions after entering the ion mobility spectrometer apparatus are also completely the same. Therefore, the reliability and accuracy of the obtained relative peak position/calibration coefficient are also higher than that of non-real-time calibration, which will not result in the need to recalibrate the apparatus due to the change of detection location, environmental temperature and humidity.

Although some embodiments of the general concept of the present disclosure have been illustrated and described, it should be understood by those ordinary skilled in the art that these embodiments may be changed without departing from the principle and spirit of the general concept of the present disclosure. The scope of the present disclosure is defined by the claims and their equivalents.

The invention claimed is:

1. A real-time calibration device used for an apparatus to be calibrated, comprising:
   a calibration agent storage tank for storing a calibration agent;
   a sealing plug arranged in the calibration agent storage tank and contacting an inner wall of the calibration storage tank to divide a space in the calibration agent storage tank into a first cavity and a second cavity, wherein the first cavity and the second cavity are arranged side by side and separated by the sealing plug, the sealing plug comprising one or more capillary through holes to allow calibration agent molecules stored in the first cavity to diffuse into the second cavity through the one or more capillary through holes of the sealing plug;
   a valve configured to open or close a passage between the second cavity of the calibration agent storage tank and a sample injection pipeline of the apparatus to be calibrated, so as to control a release of the calibration agent to the sample injection pipeline of the apparatus to be calibrated; and
   a calibration agent capsule arranged in the first cavity to store a sample containing the calibration agent so as to enable a release of the calibration agent molecules into the first cavity;
   wherein the valve is connected to the sample injection pipeline of the apparatus to be calibrated.

2. The real-time calibration device according to claim 1, wherein the valve is an electromagnetic valve configured to open for a predetermined period of time during a sample injection of the apparatus to be calibrated, so that the calibration agent storage tank releases a trace amount of calibration agent into the sample injection pipeline, the trace amount of calibration agent and a sample entering the apparatus to be calibrated are mixed and together enter the apparatus to be calibrated, and information of the sample and the calibration agent is detected by the apparatus to be calibrated, thereby performing a calibration.

3. The real-time calibration device according to claim 1, further comprising a storage tank cover connected to the storage tank and covering one end of the storage tank, wherein the valve is in fluid communication with the storage tank through a through hole provided in the storage tank cover.

4. The real-time calibration device according to claim 1, further comprising a semi-permeable membrane arranged on one end of the storage tank close to the valve, wherein the semi-permeable membrane and the sealing plug define the second cavity, and wherein the semi-permeable membrane allows the calibration agent molecules to enter the valve from the second cavity through the semi-permeable membrane.

5. The real-time calibration device according to claim 1, further comprising at least one of a first O-ring washer and a second O-ring washer, wherein the first O-ring washer is arranged between the sealing plug and an inner wall of the storage tank, so as to seal a gap between the sealing plug and the inner wall of the storage tank, and wherein the second O-ring washer is arranged between the storage tank cover and an end surface of the storage tank at one end, so as to seal the storage tank.

6. A real-time calibration method used for an apparatus to be calibrated, comprising:
   instantaneously releasing a trace amount of calibration agent molecules by using a calibration device during a sample injection of the apparatus to be calibrated, so that the trace amount of calibration agent molecules and a sample entering the apparatus to be calibrated are mixed and together enter the apparatus to be calibrated, and information of the sample and the calibration agent is detected by the apparatus to be calibrated, thereby performing a calibration, the calibration device comprising:
   a calibration agent storage tank for storing a calibration agent;
   a valve configured to open or close a passage between the calibration agent storage tank and a sample injection pipeline of the apparatus to be calibrated, so as to control a release of the calibration agent molecules into the sample injection pipeline of the apparatus to be calibrated; and a sealing plug arranged in the calibration agent storage tank to divide a space in the calibration agent storage tank into a first cavity and a second cavity located at a side of the first cavity, and the sealing plug comprises one or more capillary through holes to allow calibration agent molecules stored in the first cavity to diffuse into the second cavity through the one or more capillary through holes of the sealing plug; and opening the valve, during the sample injection of the apparatus to be calibrated, for a predetermined period of time, to release calibration agent molecules so that the calibration agent molecules and sample molecules are mixed and together enter the apparatus to be calibrated;

wherein the calibration device further comprises a calibration agent capsule arranged in the first cavity and comprising a capsule shell and calibration agent contained in the capsule shell, the capsule shell allowing the calibration agent capsule to release calibration agent molecules into the first cavity.

7. The real-time calibration method according to claim 6, wherein the calibration device further comprises a storage tank cover connected to the calibration agent storage tank and covering one end of the calibration agent storage tank, and the valve is in fluid communication with the calibration agent storage tank through a through hole provided in the storage tank cover.

8. The real-time calibration method according to claim 6, wherein the calibration device further comprises a semi-permeable membrane arranged on one end of the calibration agent storage tank close to the valve, the semi-permeable membrane and the sealing plug define the second cavity, and the semi-permeable membrane allows the calibration agent molecules to enter the valve from the second cavity through the semi-permeable membrane.

9. The real-time calibration method according to claim 6, wherein the calibration device further comprises at least one of a first O-ring washer and a second O-ring washer, wherein the first O-ring washer is arranged between the sealing plug and an inner wall of the storage tank, so as to seal a gap between the sealing plug and the inner wall of the storage tank, and wherein the second O-ring washer is arranged between the storage tank cover and an end surface of the storage tank at one end, so as to seal the storage tank.

10. The real-time calibration method according to claim 6, wherein, during an input of sample molecules of the apparatus to be calibrated, the valve is opened for a predetermined period of time to release the calibration agent molecules, so that the calibration agent molecules and the sample molecules are mixed and together enter the apparatus to be calibrated; and wherein the real-time calibration method further comprises:

obtaining measured peak position information $t_{x\ sample}$ of the sample and calibration agent peak position information $t_{c1}$;

extracting current calibration agent peak position information $t_{c1}$, comparing it with reference calibration agent peak position information to stored in a database, and calculating a ratio $C_i=(t_{c0})/(t_{c1})$ of the reference calibration agent peak position information $t_{c0}$ to the current calibration agent peak position information $t_{c1}$; and multiplying the ratio $C_i$ by the measured peak position information $t_{x\ sample}$ of the sample, and obtaining a calibrated peak position $t_{sample}$ of the sample.

11. A detection apparatus comprising a measurement device and the real-time calibration device used for the apparatus to be calibrated according to claim 1, wherein the measurement device is the apparatus to be calibrated, and wherein the real-time calibration device is in fluid communication with a sample injection pipeline of the measurement device through the valve.

12. The detection apparatus according to claim 11, wherein, during a sample injection of the measurement device, the real-time calibration device instantaneously releases a trace amount of calibration agent molecules, the trace amount of calibration agent molecules and a sample are mixed and together enter the measurement device, and information of the sample and the calibration agent is detected by the measurement device, thereby performing a calibration.

13. The detection apparatus according to claim 11, wherein the measurement device is configured to:

obtain measured peak position information $t_{x\ sample}$ of the sample and calibration agent peak position information $t_{c1}$;

extract current calibration agent peak position information $t_{c1}$, compare it with reference calibration agent peak position information to stored in a database, and calculate a ratio $C_i=(t_{c0})/(t_{c1})$ of the reference calibration agent peak position information to to the current calibration agent peak position information $t_{c1}$; and multiply the ratio $C_i$ by the measured peak position information $t_{x\ sample}$ of the sample, and obtain a calibrated peak position $t_{sample}$ of the sample.

14. The detection apparatus according to claim 11, wherein the detection apparatus is an ion mobility spectrometer apparatus, the measurement device is an ion mobility spectrometer, and the real-time calibration device is in fluid communication with the sample injection pipeline of the ion mobility spectrometer through the valve.

* * * * *